United States Patent
McCanny et al.

(10) Patent No.: US 11,672,997 B2
(45) Date of Patent: Jun. 13, 2023

(54) GUIDE SYSTEM AND METHOD FOR INDICATING A DEFIBRILLATOR ACTIVATOR

(71) Applicant: HeartSine Technologies Limited, Belfast (GB)

(72) Inventors: Paul McCanny, Newtownabbey (GB); Allister McIntyre, Newtownards (GB); Johnny Anderson, Holywood (GB)

(73) Assignee: Heartsine Technologies Limited, Belfast (GB)

( * ) Notice: Subject to any disclaimer, the term of this patent is extended or adjusted under 35 U.S.C. 154(b) by 326 days.

(21) Appl. No.: 16/219,341

(22) Filed: Dec. 13, 2018

(65) Prior Publication Data
US 2019/0192868 A1  Jun. 27, 2019

(30) Foreign Application Priority Data
Dec. 22, 2017 (GB) .................................... 1721764

(51) Int. Cl.
*A61N 1/39* (2006.01)
*A61N 1/04* (2006.01)

(52) U.S. Cl.
CPC .......... *A61N 1/3925* (2013.01); *A61N 1/3904* (2017.08); *A61N 1/3993* (2013.01); *A61N 1/046* (2013.01)

(58) Field of Classification Search
CPC ...... A61N 1/39; A61N 1/3904; A61N 1/3925; A61N 1/3993; A61N 1/02; A61N 1/025; A61N 1/046

USPC .......................................................... 607/5–8
See application file for complete search history.

(56) References Cited

U.S. PATENT DOCUMENTS

| | | | |
|---|---|---|---|
| 6,871,094 B1* | 3/2005 | Allen | A61N 1/3925 600/518 |
| 2003/0040293 A1* | 2/2003 | Fish | G11B 27/105 455/186.1 |
| 2003/0208237 A1* | 11/2003 | Locke | A61N 1/3993 607/5 |
| 2003/0216785 A1* | 11/2003 | Edwards | A61N 1/3993 607/5 |
| 2005/0251213 A1* | 11/2005 | Freeman | G09B 5/06 607/5 |
| 2006/0129191 A1* | 6/2006 | Sullivan | A61N 1/3904 607/5 |
| 2007/0127241 A1* | 6/2007 | Faunce | F21V 33/006 362/249.12 |
| 2013/0053063 A1* | 2/2013 | McSheffrey | G08B 7/066 455/456.1 |
| 2013/0304142 A1* | 11/2013 | Curtin | A61N 1/3993 607/5 |
| 2016/0148495 A1* | 5/2016 | Buchanan | A61N 1/3904 340/539.17 |
| 2017/0246466 A1* | 8/2017 | Murphy | A61N 1/3975 |
| 2017/0252571 A1* | 9/2017 | Dascoli | A61N 1/3987 |
| 2018/0169426 A1* | 6/2018 | Montague | A61H 31/00 |
| 2020/0267509 A1* | 8/2020 | Stapleford | H04W 4/20 |
| 2021/0228893 A1* | 7/2021 | Akram | A61N 1/3904 |

* cited by examiner

Primary Examiner — Ahmed M Farah

(57) ABSTRACT

A guide system for indicating an activator of a defibrillator to a user including a motion detection circuit which determines motion of the defibrillator and generates at least one defibrillator motion mode signal, and a guide circuit which receives the defibrillator motion mode signal and causes the activator to be indicated to the user of the defibrillator.

14 Claims, 2 Drawing Sheets

GUIDE SYSTEM AND METHOD FOR INDICATING A DEFIBRILLATOR ACTIVATOR

PRIORITY INFORMATION

The present application claims priority to UK patent application No. 1721764.7, filed 22 Dec. 2017, the content of which is incorporated herein by reference in its entirety.

BACKGROUND OF THE INVENTION

1. Field of the Invention

The disclosure relates to a guide system for indicating a defibrillator activator which allows a user of the defibrillator to more readily identify how to activate the defibrillator.

2. Introduction

Studies have shown that in instances of sudden cardiac arrest, prompt intervention by the application of one or more defibrillation shocks and/or cardiopulmonary resuscitation, may have a positive outcome. Defibrillators are therefore commonly found in many locations, such as shopping malls, schools, theatres, etc. Generally, once activated, a defibrillator will provide instructions on its operation and appropriate intervention to a user. This will only occur if the defibrillator is activated. A user may not be aware of the need to activate the defibrillator or a user may experience difficulty in activating the defibrillator, particularly in the circumstances of a sudden cardiac arrest.

SUMMARY

Additional features and advantages of the disclosure will be set forth in the description which follows, and in part will be obvious from the description, or may be learned by practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth herein.

According to a first aspect of the disclosure there is provided a guide system for indicating an activator of a defibrillator to a user including: a motion detection circuit which determines motion of the defibrillator and generates at least one defibrillator motion mode signal, and a guide circuit which receives the defibrillator motion mode signal and causes the activator to be indicated to the user of the defibrillator. A second aspect of this disclosure includes a method embodiment which involves using a motion detection circuit to determine appropriately if the defibrillator is moving and to provide an activation notification to the user according to a guide circuit when the defibrillator is moving in a way that indicates use rather than transportation of the defibrillator.

BRIEF DESCRIPTION OF THE DRAWINGS

In order to describe the manner in which the above-recited and other advantages and features of the disclosure can be obtained, a more particular description of the disclosure briefly described above will be rendered by reference to specific embodiments thereof which are illustrated in the appended drawings. Understanding that these drawings depict only exemplary embodiments of the disclosure and are not therefore to be considered to be limiting of its scope, the disclosure will be described and explained with additional specificity and detail through the use of the accompanying drawings in which.

DETAILED DESCRIPTION

Figure 1:
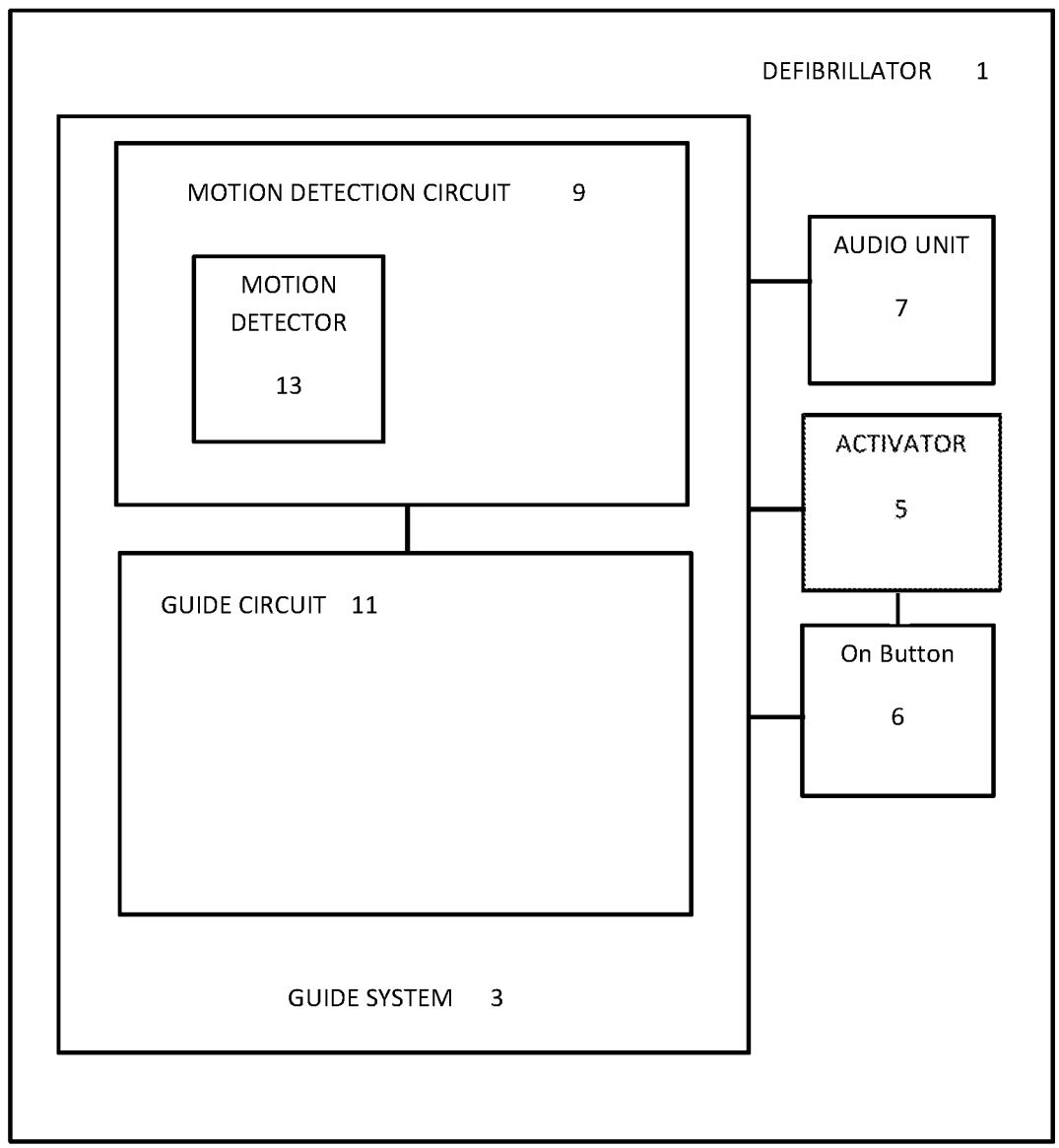
FIG. 1 illustrates a defibrillator according to an aspect of this disclosure.

An embodiment of the disclosure will now be described by way of example only with reference to the accompanying FIG. 1 which is a schematic representation of a guide system according to the first aspect of the disclosure included in a defibrillator.

Referring to the figure, a defibrillator 1 includes a guide system 3 for indicating an activator of the defibrillator to a user, an activator 5, in the form of an ON button 6, and an audio unit 7. It will be appreciated that the defibrillator includes other components such as electrodes, defibrillation shock circuitry, etc. which are not shown.

The guide system 3 includes a motion detection circuit 9 and a guide circuit 11. The motion detection circuit 9 includes a motion detector 13, in the form of an accelerometer, but could include other types of motion detectors. The guide system 3 is connected to the activator 5 and the audio unit 7 for sending signals thereto.

Generally, the defibrillator 1 will be transported to its assigned location in, for example, a school, and installed within a housing (not shown). The defibrillator 1 remains substantially immobile within the housing until it is required. When the defibrillator 1 is required, it is removed from its housing by a user, for example for use in a sudden cardiac arrest event. The guide system 3 of the defibrillator 1 distinguishes motion of the defibrillator by the user from other motion of the defibrillator, such as transport of the defibrillator, and causes the activator 5 of the defibrillator 1 to be indicated to the user.

The motion detection circuit 9 determines motion of the defibrillator 1 by the user by determining substantial immobility of the defibrillator 1 over a pre-determined period of time followed by determining motion of the defibrillator 1. Additionally, the motion detection circuit 9 may determine motion of the defibrillator 1 by the user by determining simultaneous motion of the defibrillator 1 in at least two directions using the motion detector accelerometer 13. On determination of motion of the defibrillator 1, the motion detection circuit 9 generates at least one defibrillator motion mode signal.

The guide circuit 11 receives the defibrillator motion mode signal, caused by motion of the defibrillator 1 by the user, and generates an indication signal having a square waveform which is sent to the activator 5 of the defibrillator 1. The signal causes the defibrillator activator 5 to repeatedly flash. The guide circuit 11 generates a further indication signal and sends this to the audio unit 7 of the defibrillator 1. The signal causes the audio unit to issue an audio prompt indicating the activator 5 to the user of the defibrillator 1. Thus the guide system 3 of the disclosure guides the user to the activator 5 of the defibrillator 1 by flashing of the activator and by an audio prompt.

The motion detection circuit can include a motion detector including any of an accelerometer, a mercury tilt switch, a magnetic motion sensor, a capacitance motion sensor.

The motion detection circuit may determine motion of the defibrillator by the user and generate the at least one defibrillator motion mode signal. The motion detection circuit may determine motion of the defibrillator by the user by determining substantial immobility of the defibrillator over a pre-determined period of time followed by determining motion of the defibrillator. Additionally or alternatively, the motion detection circuit may determine motion of the defibrillator by the user by determining simultaneous motion of the defibrillator in at least two directions. The motion detection circuit may determine simultaneous motion of the defibrillator in at least two directions by using an accelerometer.

The motion detection circuit is therefore able to distinguish motion of the defibrillator by a user from other motion of the defibrillator such as transport of the defibrillator.

The guide circuit may generate an indication signal and send the indication signal to the activator which causes the activator to be indicated to the user of the defibrillator. The guide circuit may generate an indication signal having a waveform which causes the activator to be illuminated and remain illuminated. The guide circuit may generate an indication signal having a waveform which causes the activator to repeatedly flash or perform some other signal. The guide circuit may generate an indication signal having a waveform which causes the activator to repeatedly gradually increase from a minimum illumination to a maximum illumination and then decrease from the maximum illumination to the minimum illumination.

The guide circuit may send the indication signal to the activator for a pre-determined period of time. The guide circuit can include a timer which times sending of the indication signal to the activator and enables sending to be ceased at the end of the pre-determined period of time or until activation of the defibrillator. The pre-determined period of time may be approximately 10 seconds or some other time frames. The pre-determined period of time may be chosen to limit power consumption of the defibrillator.

The guide circuit may generate a further indication signal and send the further indication signal to an audio unit of the defibrillator which causes the audio unit to issue an audio prompt indicating the activator to the user of the defibrillator.

According to a second aspect of the disclosure there is provided a method for indicating an activator of a defibrillator to a user. In one aspect, the method includes using a motion detection circuit to determine whether the defibrillator is moving and to generate at least one defibrillator motion movement signal. The method includes using a guide circuit to receive the defibrillator movement mode signal and cause a notice to be provided to the user of the defibrillator.

Figure 2:
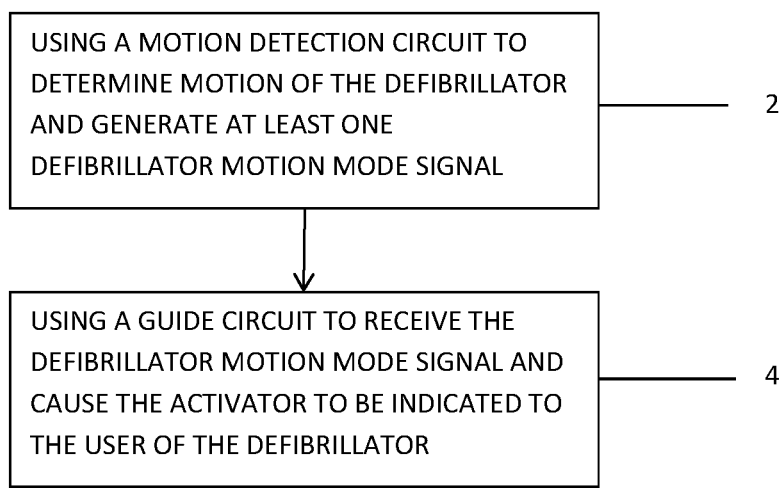
FIG. 2 illustrates a method aspect of this disclosure.

FIG. 2 illustrates another method aspect of this disclosure. A method in this regard includes one or more of the steps of using a motion detection circuit to determine motion of the defibrillator and/or generate at least one defibrillator motion mode signal (2), and using a guide circuit to receive the defibrillator motion mode signal and/or cause an activator to be indicated to the user of the defibrillator (4). The activator can be visual, audible, haptic, textual, graphical, or any combination of these modes of communication.

Whether to practice the method or in connection with the defibrillator embodiment, where necessary, computer components are included within the scope of this disclosure. Such components can include, without limitation, a processor, a bus that communicates data between computer components, an input component, an output component, graphical user interfaces, speech processing or speech related components, multi-modal input components, various modules which include computer code programmed to cause the processor to perform certain functions as disclosed herein, or non-transitory computer-readable devices that store computer code or computer-implemented instructions, which, when implemented, cause a processor or a specific module to perform certain operations.

We claim:

1. A guide system for indicating an activator of a defibrillator to a user comprising:
   an activator integrated with a defibrillator, the activator comprising an on button;
   a motion detection circuit, integrated into the defibrillator, which determines motion of the defibrillator and generates at least one defibrillator motion mode signal; and
   a guide circuit, integrated into the defibrillator, which receives the defibrillator motion mode signal and causes the activator to be indicated to the user of the defibrillator by illuminating the activator, wherein, when the user interacts with the on button, the on button causes the defibrillator to start.

2. A system according to claim 1, in which the motion detection circuit comprises a motion detector comprising of any of an accelerometer, a mercury tilt switch, a magnetic motion sensor, a capacitance motion sensor.

3. A system according to claim 1, in which the motion detection circuit determines motion of the defibrillator by the user and generates the at least one defibrillator motion mode signal.

4. A system according to claim 3, in which the motion detection circuit determines motion of the defibrillator by the user by determining simultaneous motion of the defibrillator in at least two directions.

5. A system according to claim 4, in which the motion detection circuit determines simultaneous motion of the defibrillator in at least two directions by using an accelerometer.

6. A system according to claim 1, in which the motion detection circuit determines motion of the defibrillator by the user by determining immobility of the defibrillator over a pre-determined period of time followed by determining motion of the defibrillator.

7. A system according to claim 1, in which the guide circuit generates an indication signal and sends the indication signal to the activator which causes the activator to be indicated to the user of the defibrillator.

8. A system according to claim 7, in which the guide circuit generates the indication signal having a waveform which causes the activator to be illuminated and remain illuminated.

9. A system according to claim 7, in which the guide circuit generates the indication signal having a waveform which causes the activator to repeatedly flash.

10. A system according to claim 7, in which the guide circuit generates the indication signal having a waveform which causes the activator to repeatedly gradually increase from a minimum illumination to a maximum illumination and then decrease from the maximum illumination to the minimum illumination.

11. A system according to claim 7, in which the guide circuit sends the indication signal to the activator for a pre-determined period of time.

12. A system according to claim 11, in which the guide circuit comprises a timer which times sending of the indication signal to the activator and enables sending to be ceased at an end of the pre-determined period of time or until activation of the defibrillator.

13. A system according to claim 11, in which the pre-determined period of time is approximately 10 seconds.

14. A system according to claim 7, in which the guide circuit generates a further indication signal and sends the further indication signal to an audio unit of the defibrillator which causes the audio unit to issue an audio prompt indicating the activator to the user of the defibrillator.

* * * * *